US00RE46101E

(19) United States
(12) Reissued Patent
Stewart

(10) Patent Number: US RE46,101 E
(45) Date of Reissued Patent: Aug. 16, 2016

(54) FLUID CONDITIONING APPARATUS

(71) Applicant: Fuel Vapor Systems, Inc., Englewood, CO (US)

(72) Inventor: Peter Robert Stewart, Fife (GB)

(21) Appl. No.: 14/220,884

(22) Filed: Mar. 20, 2014

Related U.S. Patent Documents

Reissue of:
(64) Patent No.: 8,136,798
Issued: Mar. 20, 2012
Appl. No.: 11/971,907
Filed: Jan. 10, 2008

(51) Int. Cl.

| | |
|---|---|
| ***B01D 53/34*** | (2006.01) |
| ***A61L 9/14*** | (2006.01) |
| ***B01D 53/38*** | (2006.01) |
| ***B01D 53/79*** | (2006.01) |
| ***A61L 9/00*** | (2006.01) |

(52) U.S. Cl.
CPC ... *A61L 9/14* (2013.01); *A61L 9/00* (2013.01); *B01D 53/38* (2013.01); *B01D 53/79* (2013.01)

(58) Field of Classification Search
CPC ..... A61L 19/14; B01D 53/38; B01D 53/79
USPC ..... 261/19, 76, 78.1, 115; 95/1, 8, 149; 96/234, 244, 251; 210/739, 749, 143, 210/198.1; 422/3, 4, 105, 168, 120
See application file for complete search history.

(56) References Cited

U.S. PATENT DOCUMENTS

| | | | | |
|---|---|---|---|---|
| 4,467,844 | A | | 8/1984 | Di Gianfilippo et al. |
| 4,844,874 | A | | 7/1989 | deVries |
| 4,963,330 | A | | 10/1990 | Johansson et al. |
| 5,025,642 | A | | 6/1991 | Brunskill et al. |
| 5,030,253 | A | | 7/1991 | Tokuhiro et al. |
| 5,159,835 | A | | 11/1992 | Nafziger et al. |
| 5,214,935 | A | | 6/1993 | Brunskill |
| 5,223,230 | A | | 6/1993 | Takemura et al. |
| 5,302,359 | A | | 4/1994 | Nowatzki |
| 5,380,498 | A | | 1/1995 | Kuivalainen |
| 5,620,503 | A | * | 4/1997 | Miller et al. ..... 95/211 |
| 5,667,651 | A | * | 9/1997 | Bryan ..... 204/401 |
| 5,693,293 | A | | 12/1997 | Reichardt et al. |
| 5,720,926 | A | * | 2/1998 | Whipp et al. ..... 422/110 |
| 5,989,497 | A | | 11/1999 | Labonte |
| 6,155,255 | A | | 12/2000 | Lambert |
| 6,435,419 | B1 | | 8/2002 | Davis |
| 6,548,025 | B1 | | 4/2003 | Rasouli et al. |
| 6,555,053 | B1 | | 4/2003 | Aoyagi |
| 6,604,493 | B1 | | 8/2003 | Toki |
| 6,770,247 | B1 | | 8/2004 | Romack et al. |
| 6,964,699 | B1 | * | 11/2005 | Carns et al. ..... 96/361 |
| 7,008,592 | B2 | | 3/2006 | Sias et al. |
| 7,014,813 | B1 | * | 3/2006 | Watling et al. ..... 422/26 |
| 7,032,893 | B2 | | 4/2006 | Sotoyama et al. |

(Continued)

*Primary Examiner* — Terrence Till
(74) *Attorney, Agent, or Firm* — Roger A. Jackson

(57) ABSTRACT

An apparatus and method for a fluid conditioning apparatus for conditioning a fluid disposed within, wherein the fluid conditioning apparatus is in fluid communication with a self contained system. The fluid conditioning apparatus includes a housing having a surrounding sidewall positioned about a longitudinal axis, the surrounding sidewall having an inlet portion and an outlet portion, the sidewall, inlet portion, and outlet portion all defining a housing interior. Further included in the fluid conditioning apparatus is structure for disbursing a selected component within the housing interior and structure for controlling the selected component disbursing to a achieve a selected fluid condition.

7 Claims, 13 Drawing Sheets

(56) References Cited

U.S. PATENT DOCUMENTS 7,077,884 B2 * 7/2006 Davis et al. ..... 95/8
7,850,931 B2 * 12/2010 McDonnell et al. ..... 422/292
2005/0188841 A1 * 9/2005 Khan ..... 95/8
2007/0079799 A1 4/2007 Scouten
2007/0098592 A1 * 5/2007 Buczynski et al. ..... 422/3
2007/0283814 A1 12/2007 Thom

* cited by examiner

FLUID CONDITIONING APPARATUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention generally relates to an apparatus for conditioning a fluid for the purpose of adding and/or removing a component and/or desirably chemically altering the undesirable component within the fluid for an adjacent system. More particularly the present invention is an apparatus that includes a fluid mover, and selectable component adder, and a control to achieve the desired fluid properties for the adjacent system.

BACKGROUND OF INVENTION

There are many processes that require a form of fluid conditioning in chemical processing plants, oil refineries, factories, food processing, farm and animal byproduct processing, wastewater treatment, solid waste treatment, and the like. As these aforementioned processes are usually necessarily for our modern economy, technology is usually applied to control the undesirable environmental contaminates generated from the previously mentioned processes for a number of reasons, with these contaminants being in gaseous form, in liquid form, or in solid form. These reasons would include reduction of physical pollutants, reduction of visible pollutants, reduction of odorous contaminants, reduction of chemical contaminants, and the like. As the concern for the environment continues to increase it becomes ever more important to control these contaminants to lower and lower acceptable levels.

This issue of industrial process contaminant control has been fairly well recognized in the prior art with a number of apparatus designed for contaminant treatment that include conventional filtering systems, and other more technologically adept systems such as scrubbers that are typically used with a contaminated gas stream, wherein a chemical is introduced into the gas stream to bond with an undesirable contaminant in the gas stream, wherein the bonding results in typically a new solid being formed that can precipitate out of the gas stream due to its higher density allowing for separation of the contaminant out of the gas stream. Another prior art gas contaminant process involves what is called electrostatic precipitation, wherein the suspended contaminants are ionized, with the ionized contaminants being attracted to an electrode, thus enabling the separation of the contaminants from the gas stream. However, all of the aforementioned systems have limitations, such as conventional filtering not having the ability to remove very small contaminants or well dispersed contaminants, plus temperature and pressure limitations, along with high maintenance, i.e. filter cleaning/replacement required. Further, scrubbers are limited by needing to be used with a closed loop system, i.e. contained within a series of enclosures separated from the outside environment, which precludes open type systems such as some wastewater and solid waste treatment processes, in addition scrubbers require that the contaminant be able to bond with an introduced chemical with and form some sort of matter having a density higher than the gas being treated to allow separation of the contaminate from the gas being treated. In addition, for electrostatic precipitators, much the same as for scrubbers a closed loop system would be required as previously discussed and there would be the need for the contaminate to be ionizable to facilitate the electrostatic attraction of the contaminate out of the polluted gas stream.

Another type of fluid decontamination is with the use of introducing a desirable odor containing fluid to mask or cover-up an undesirable odor, thus not having the requirements of using the closed loop system as previously described nor that the contaminant have some sort of special properties to enable the separation of the contaminant from the polluted gas for instance. However, this introduction of a cover-up type of chemical has drawbacks in control over the system that is being decontaminated as the actual removal or neutralization of contaminates is not necessarily known, at least making the cover-up type of chemical fluid decontamination apparatus less desirable when used in conjunction with the open type system because of this lack of control as previously discussed. Also, because of the random interaction of the desirable odor containing fluid with the polluted gas, there is the ongoing problem of insufficient atomization of the introduced odor containing fluid within the polluted gas, thus the prior art has recognized this issue and has developed several structures to help improve atomization of the introduced fluid being dispersed within the polluted gas for more efficient odor control and less waste of the non atomized introduced fluid.

As a prior art example in addressing the need for improved atomization of the introduced fluid, in U.S. Pat. No. 6,770,247 B1 to Romack et al., disclosed is a liquid product vaporizing apparatus for an air deodorizing system comprising an inlet channel, a vaporization chamber, an air blower, and distribution pipes. In Romack et al., fresh air is drawn into the system through the inlet channel by the air blower, creating a stream of air flowing through the system. The stream of air in Romack et al., is directed to the vaporization chamber where an atomizing nozzle sprays atomized liquid product into the vaporization chamber. The treated air stream in Romack et al., then flows through distribution pipes to a plurality of vapor release ports which allow the treated air to be released into the malodorous area, reference column 3, lines 12-25. The main issues in Romack et al., are that the chamber configuration has no internal obstructions between the inlet and outlet ports; also it is utilized in an open system, i.e. taking in ambient air for the Romack et al., inlet being in not being from a closed system. In addition, Romack et al., does not teach the use of a control system for achieving a selected an odor reduction level or the ability to maintain an odor level, furthermore Romack et al., does not address use in hazardous environments, i.e. explosive gases being present and the like.

A further prior art example for a conventional air freshener (not being a scrubber or electrostatic precipitator) is in U.S. Pat. No. 6,435,419 to Davis that discloses a liquid air freshener dispensing device for a building ventilation duct being removably attachable to the duct, wherein the entire Davis system would be considered an open loop system as the building volumetric portion is not sealed. In Davis, the duct is in communication with a heating member and a blowing member, wherein the blowing member blows air across the heating member and into the duct including a coalescing filter to help prevent the air freshener droplets from collecting on the plenum walls as a method to further help the recognized problem of adequate atomization of the deodorant liquid in the gas plenum. Again in Davis, there is no teaching related to a control system for monitoring deodorant use and effective odor control in the building air volume nor use in hazardous (explosive or toxic) environments. Similar to Davis in U.S. Pat. No. 5,302,359 to Nowatzki is an apparatus used for building duct ventilation systems that is a self contained unit that utilizes a reservoir, a pump, and a dispenser for dispersing the liquid deodorant with a switch that resides on top of the ventilation duct. Nowatzki also has no disclosure related to a control system for sensing the odor levels and adjusting the amount of deodorizing fluid input.

In addition, also similar to Davis and Nowatzki, in being an air deodorizer for building type applications, in U.S. Pat. No. 5,030,253 to Tokuhiro et al., disclosed is a fragrant air supply system by using a mist generating means by either air velocity of ultrasonic means. In Tokuhiro et al., the purpose is to add fragrance, rather that remove contaminants, Tokuhiro et al., does have the features of a controller for measuring the concentration of fragrance, see FIGS. 6 and 7, wherein the controller regulates the flow of the fragrance liquid and air flow into the chamber based upon the measured concentration of the fragrance. Also, included in Tokuhiro et al., is a chamber drain to recycle liquid fragrance into the liquid fragrance reservoir that is caught by the end face 41 that removes un-evaporated mist from the fragranced air. As Tokuhiro et al., is an open loop system in that only the output concentration of fragranced air is measured and controlled as the fragranced air is sent to the building interior, with no feedback or return of air possible for recycling into the system, thus the only control is for the detection and non-detection of fragranced air within the building, again see FIGS. 6 and 7. A similar type apparatus again for deodorizing, utilizing chlorite compounds is disclosed in U.S. Pat. No. 5,989,497 to Labonte Jr. that teaches a process and apparatus for deodorizing malodorous substances with specifically a chlorine dioxide-containing composition. The apparatus in Labonte, Jr., comprises a reservoir for supplying a concentrated deodorizing liquid, a means for supplying water for diluting the aqueous deodorizing liquid, an eductor for mixing the dilution water supplied and the deodorizing liquid supplied, a means for controlling the amount of the deodorizing solution, and a plurality of spray nozzles for spraying the deodorizing solution, reference column 2, lines 37-46. Note that Labonte, Jr., is also an open system primarily designed for sewers, solid waste dumps, landfills, waste lagoons, and the like. Labonte, Jr., does have some mention of a control system via the use of a monitor to detect for instance the level of hydrogen sulfite on whether to continue or stop the system and to select the amount of deodorizing liquid to be used, i.e. being a higher or lower flowrate. Further, note that Labonte, Jr., does not address use in explosive or toxic environments.

Continuing, in looking at a typical prior art scrubber as shown in U.S. Pat. No. 4,844,874 to deVries disclosed is a method and means for controlling a mist scrubbing process in which a gas containing odorous and acidic contaminants are contacted in a reaction chamber with tiny droplets of an aqueous reagent to react with and destroy the contaminants. In deVries, although this is an open system also, however, having monitoring based on measuring chemical properties of the spent contaminated mist and scrubbed gas output. Specifically, in deVries the control system measures pH of the spent stray liquid settling at the bottom of the chamber to control the flow of a "base" chemically speaking, with this being in addition to a measurement of the acidic component of the scrubbed gas leaving the reaction chamber to control the rate at which an oxidizing agent is injected into the system. As previously discussed in scrubber systems such as deVries, there is little concern for complete atomization of the injected mist solution as there is expected to be residual liquid mist solution at the bottom of the chamber that is used to ensure bonding with the with the contaminants, i.e. more mist is available than contaminants need to bond with, in an attempt to have more complete scrubbing, in conjunction with the injected mist having a "once through" application in its potential bonding contact with the gas contaminants and is not recycled, however, as stated previously the residual mist solution is measured for pH.

Further, in looking at the prior art in this area for another open system that generates an open mist of decontaminant, reference U.S. Pat. No. 7,008,592 to Sias et al. wherein disclosed is a decontamination apparatus method using an activated cleaning fluid mist for decontamination of environments and open or exposed articles from microbiological organisms. The Sias et al., apparatus comprises a cleaning fluid, a mist generator having an input flow of the cleaning fluid and an output flow of a mist of the cleaning fluid that contains ions, from an activator to activate the cleaning fluid mist that is operational to help increase efficiency of the decontamination process by the activated decontaminant entering into a redox reaction with the microbiological contaminant, reference column 1, lines 62-64, column 2, lines 20-26, and column 5, lines 50-60. Next, in U.S. Pat. No. 6,548,025 B1 to Rasouli et al., disclosed is another open loop odor generator utilizing a disc with a porous substrate having a releasable aroma that reacts to a control system signal that allows a variety of scents to be disbursed from a single disc thereby allowing a computer connected to the internet to send a signal to the odor generator to generate a selected scent from a remote location. Thus in Rasouli et al., per se the control is not for overcoming a contaminant, however, being for a selected scent sampling from a remote location.

Continuing, in U.S. Pat. No. 5,380,498 to Kuivalainen disclosed is an apparatus for the purification of waste gases that includes the use of reagents or absorbent, wherein a "wet" zone recycles the wetting zone particles that have been separated from the from the gas outside of the wetting zone chamber by first introducing the contaminated gases into the wetted zone of the chamber with the absorbent or reagent in suspension. Wherein in Kuivalainen, next the wet chamber mixture of the contaminated gas and absorbents and reagents moves to a dry chamber portion to dry the wetted particles from the wet zone with the goal being to re-carry the particles that are unreacted back into the wet zone to increase the efficiency of the reaction process. There is no teaching in Kuivalainen related to an active control system to regulate the amount of transition between the wet and dry zones or the amount of absorbents or reagents to introduce into the system, there is some specific test data related to empirical reactions using the apparatus, however, no ongoing control of the process is disclosed.

In addressing another area, in U.S. Pat. No. 4,963,330 to Johansson et al., disclosed in a method and apparatus for treating contaminated gasses having a multi medium nozzle that allows multiple fluids to be used in a single nozzle, that can be utilized for multiple chemical injections simultaneously or if desired using one of the nozzle fluid feeds to act as a cleaning agent for the nozzle that has undesirable deposits from another injected fluid.

What is needed is a fluid conditioning apparatus that is operable for the control of a closed loop system having feedback on contamination levels for a process with the ability to adjust the fluid injection rate and/or process fluid treatment flowrates to control the process contamination levels to a selected level, in addition with the capability for the fluid conditioning apparatus to be operable in hazardous or toxic environments, either for the closed loop process itself or the external environment that the fluid conditioning apparatus is in. Thus, the fluid conditioning apparatus could have the ability to operate in an intrinsically safe manner with the controls in place to set the amount of fluid injected, timing intervals for fluid injection, and have a mechanism to motivate the system fluid to be conditioned at a selected flowrate until a selected de contamination level is reached for the associated process. Further, it would be desirable to provide for removal of a portion of the un-atomized fluid injection from the process fluid stream to ensure a higher efficiency of the fluid injection de-contaminating the process in a shorter time period. In addition, the fluid conditioning apparatus should be skidded as a unit including the control system for potential portability to be in fluid communication with a multitude of selected systems that need fluid de-contamination from their associated processes.

SUMMARY OF INVENTION

Broadly, the present invention is a fluid conditioning apparatus for conditioning a fluid disposed within, wherein the fluid conditioning apparatus is in fluid communication with a self contained system. The fluid conditioning apparatus includes a housing having a surrounding sidewall positioned about a longitudinal axis, the surrounding sidewall having an inlet portion and an outlet portion, the sidewall, inlet portion, and outlet portion all defining a housing interior. Further included in the fluid conditioning apparatus is a means for disbursing a selected component within the housing interior and a means for controlling the selected component disbursing to a achieve a selected fluid condition.

These and other objects of the present invention will become more readily appreciated and understood from a consideration of the following detailed description of the exemplary embodiment(s) of the present invention when taken together with the accompanying drawings, in which;

REFERENCE NUMBERS IN DRAWINGS

Figure 1:
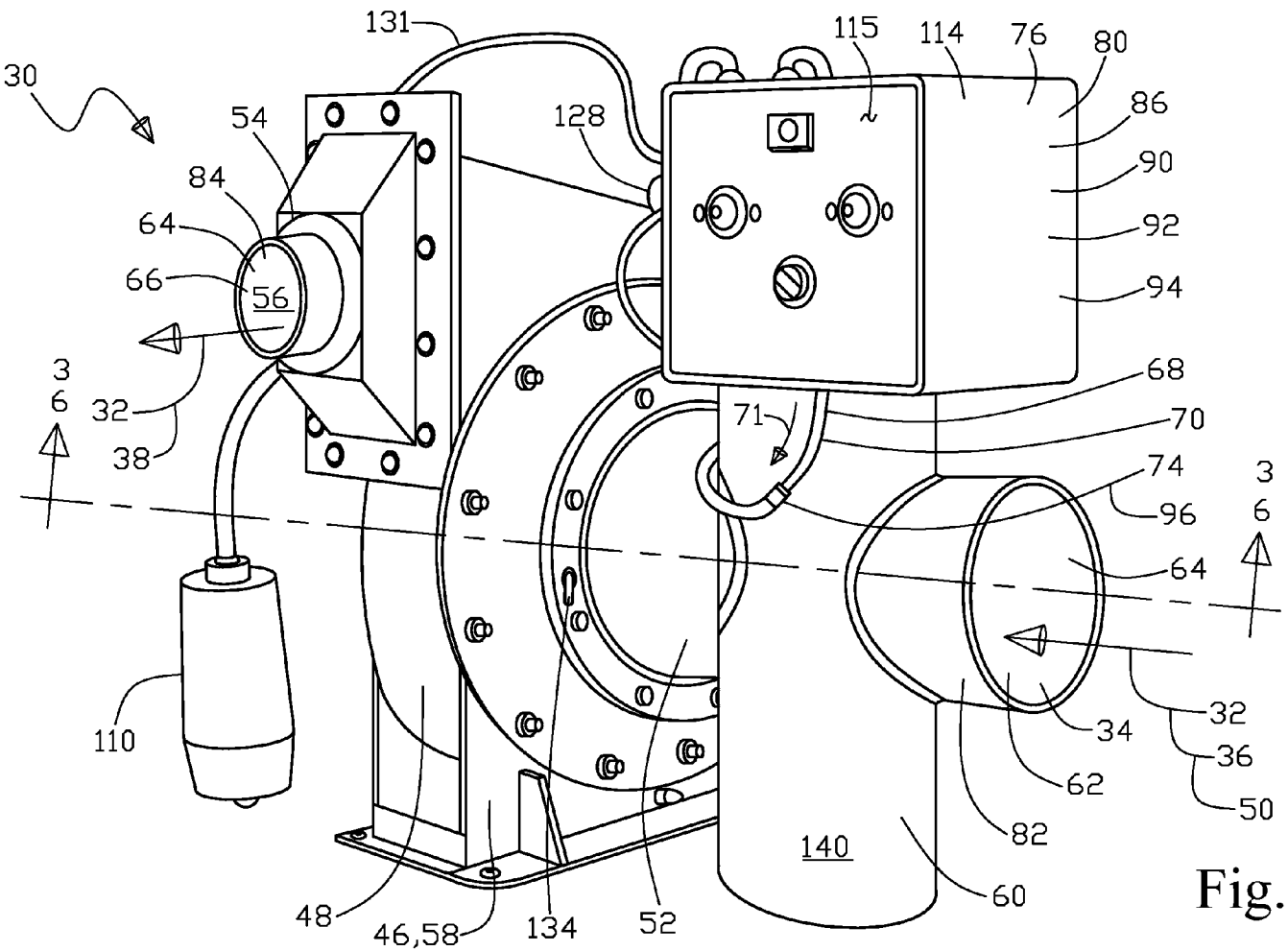
FIG. 1 shows a perspective view of the fluid conditioning apparatus.

30 Fluid conditioning apparatus
32 Fluid being selectably conditioned from the vessel 142
34 Selected fluid 32 condition
36 Incoming fluid 32 condition
38 Outgoing fluid 32 condition
40 Decontamination rate of the system
42 Fluid communication (CP)
44 Self contained system
46 Housing
48 Surrounding sidewall of housing 46
50 Longitudinal axis of housing 46
52 Inlet portion of the housing 46 surrounding sidewall 48
54 Outlet portion of the housing 46 surrounding sidewall 48
56 Interior of housing
58 Closed loop fluid duct
60 Conditioning portion of duct 58 (A)
62 Contamination portion of duct 58
64 Monitoring portion of duct 58
66 Testing portion of duct 58
68 Selected component
70 Selected fluid of the selected component 68 (CO)
71 Flow direction of selected fluid 70
72 Source of selected fluid 70 (CS)
74 Means for disbursing the selected component 68
76 Means for controlling the selected component 68
78 Means for producing a selected gas pressure and flow
80 Means for monitoring the fluid 32
82 Monitoring the fluid 32 adjacent to the inlet portion 52
84 Monitoring the fluid 32 adjacent to the outlet portion 54
86 Control for adjusting the selected fluid 70
88 Atomization rate of selected fluid 70
90 Determining a volume disbursed of the selected component 68 or liquid 70
92 Cycling or pulsing of the selected component 68 disbursing volume 90
94 Determining an allowable fluid 32 flowrate
96 Injector (H)
98 Fluid communication of injector 96
100 Means for moving the fluid 32
102 Means for moving the fluid 32 disposed within the duct 58 (B)
104 Anti-static element
106 Fan
108 Gas motor (G)
110 Sound attenuation for the gas motor 108
111 Flow direction of the gas
112 Air supply (AS)
114 Enclosure body (C)
115 Enclosure cover (C)
116 Power switch
118 Air timers
119 Pump—gas/liquid
120 Pilot valve
122 Air supply compressor
124 Primary air control (D)
126 First regulated air supply
128 Second regulated air supply (E)
130 Controlled air supply to injector nozzle 96 (AO)
131 First air control to power motor 108 (RA1)
132 Secondary air control to enclosure 114 and 115 components including pump 119, air timer 118, and power switch 116 (RA2)
134 Earth point (EP)
136 Sample points (SP)
138 Support structure
140 Suction drum
142 Vessel
144 Vessel inlet portion
146 Vessel outlet portion

DETAILED DESCRIPTION

Figure 2:
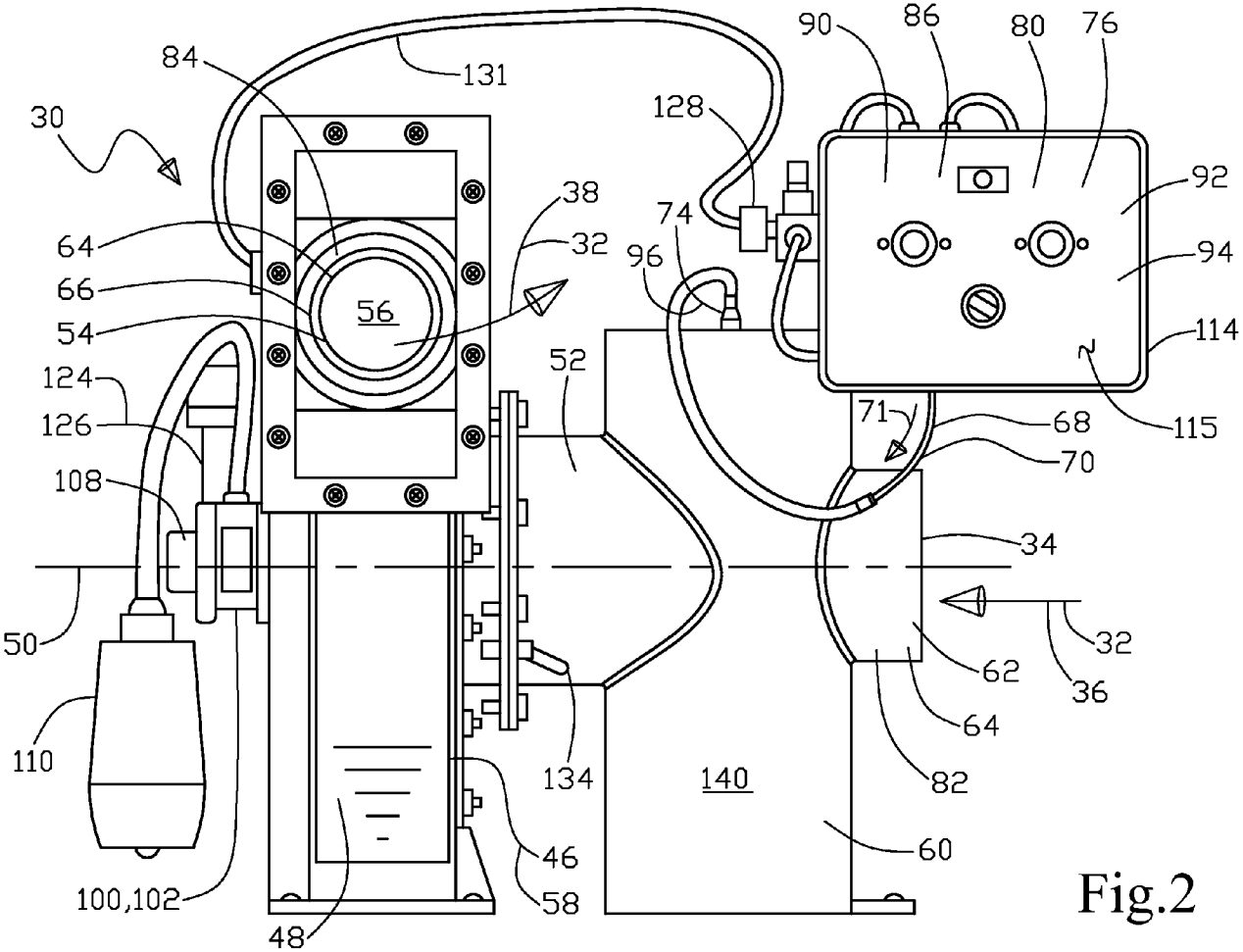
FIG. 2 shows a side elevation view of the fluid conditioning apparatus.
Figure 3:
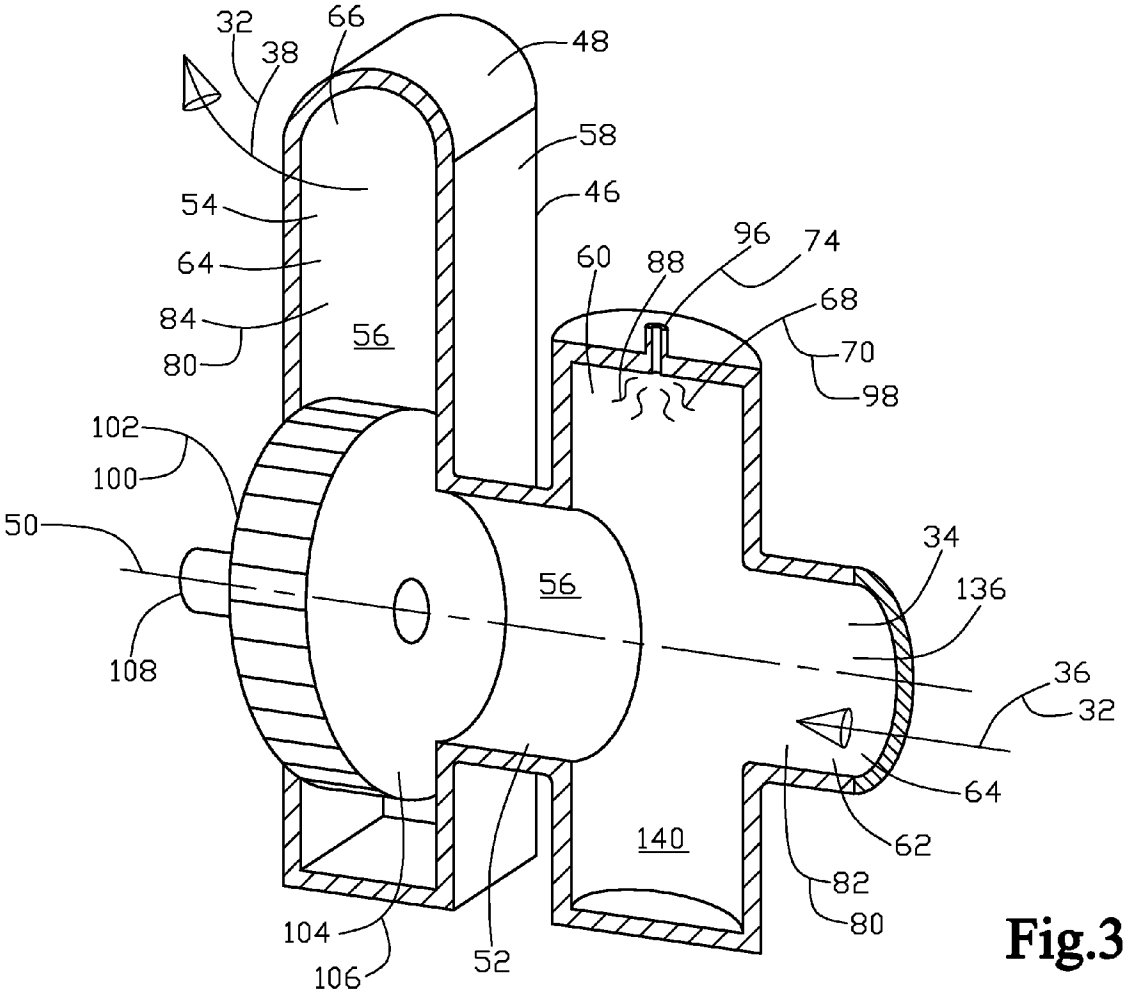
FIG. 3 shows a cross sectional perspective view 3-3 from FIG. 1 of the fluid conditioning apparatus.
Figure 4:
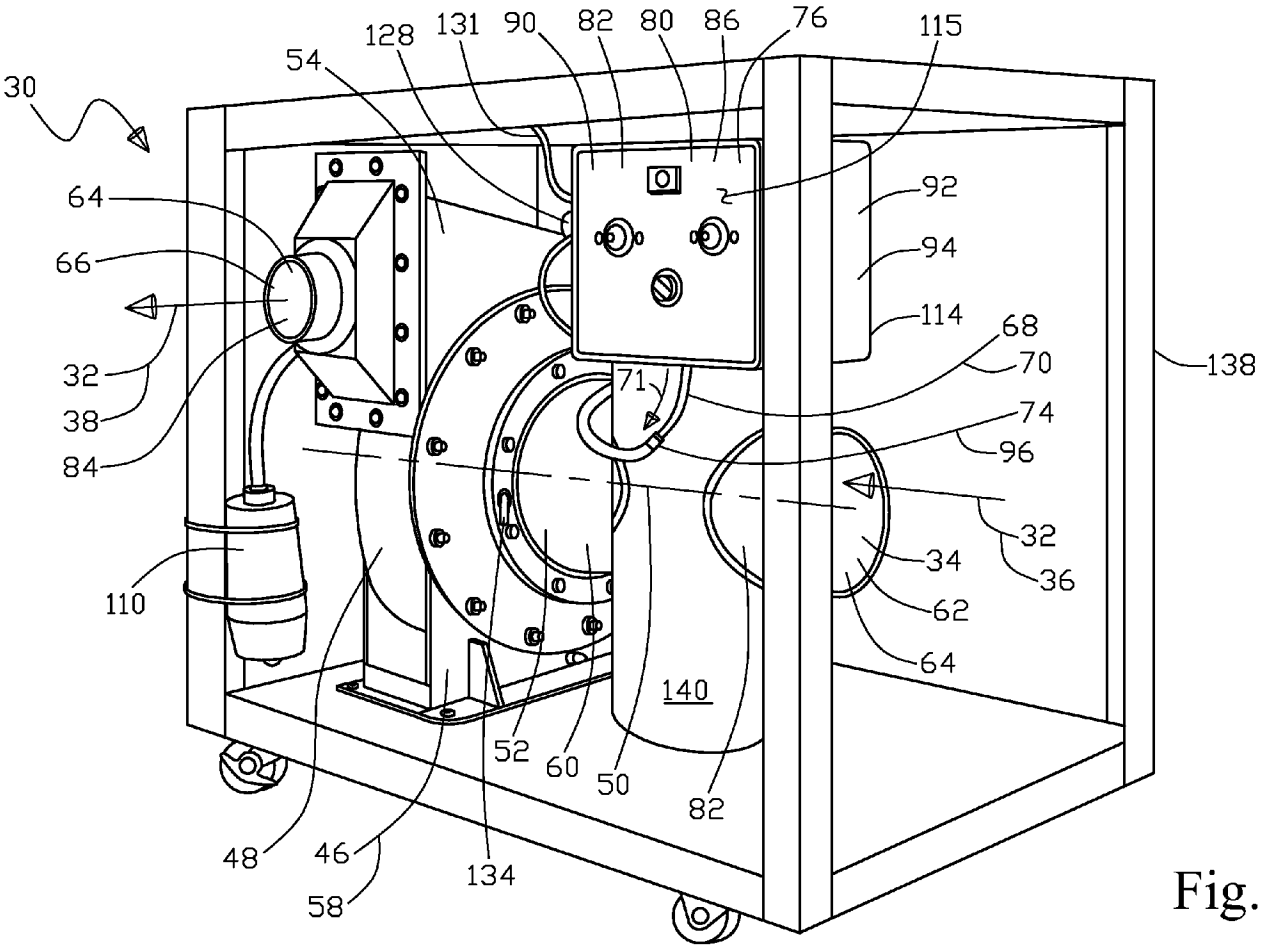
FIG. 4 shows a perspective view of the fluid conditioning apparatus including the support structure.
Figure 5:
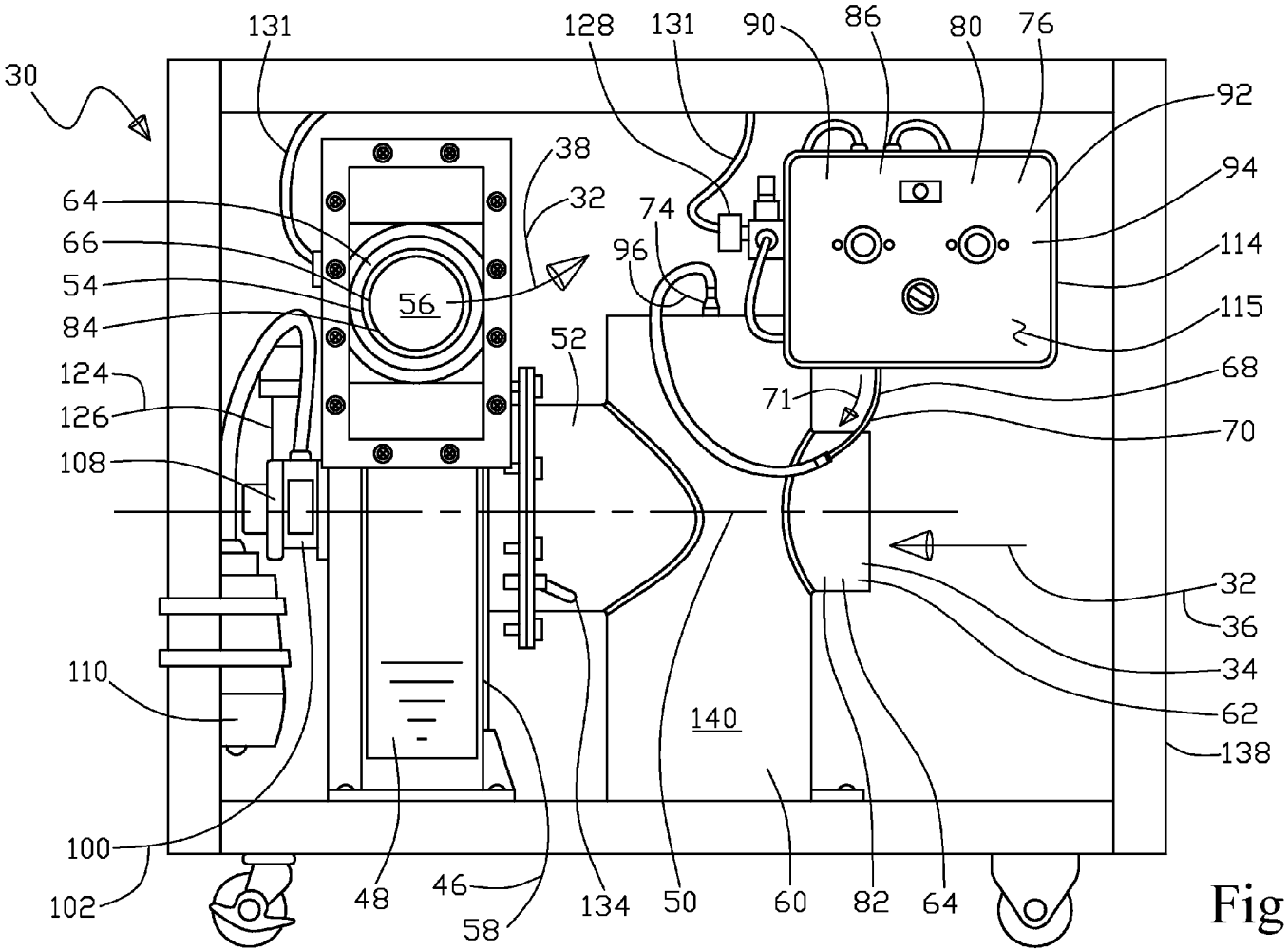
FIG. 5 shows a side elevation view of the fluid conditioning apparatus including the support structure.
Figure 6:
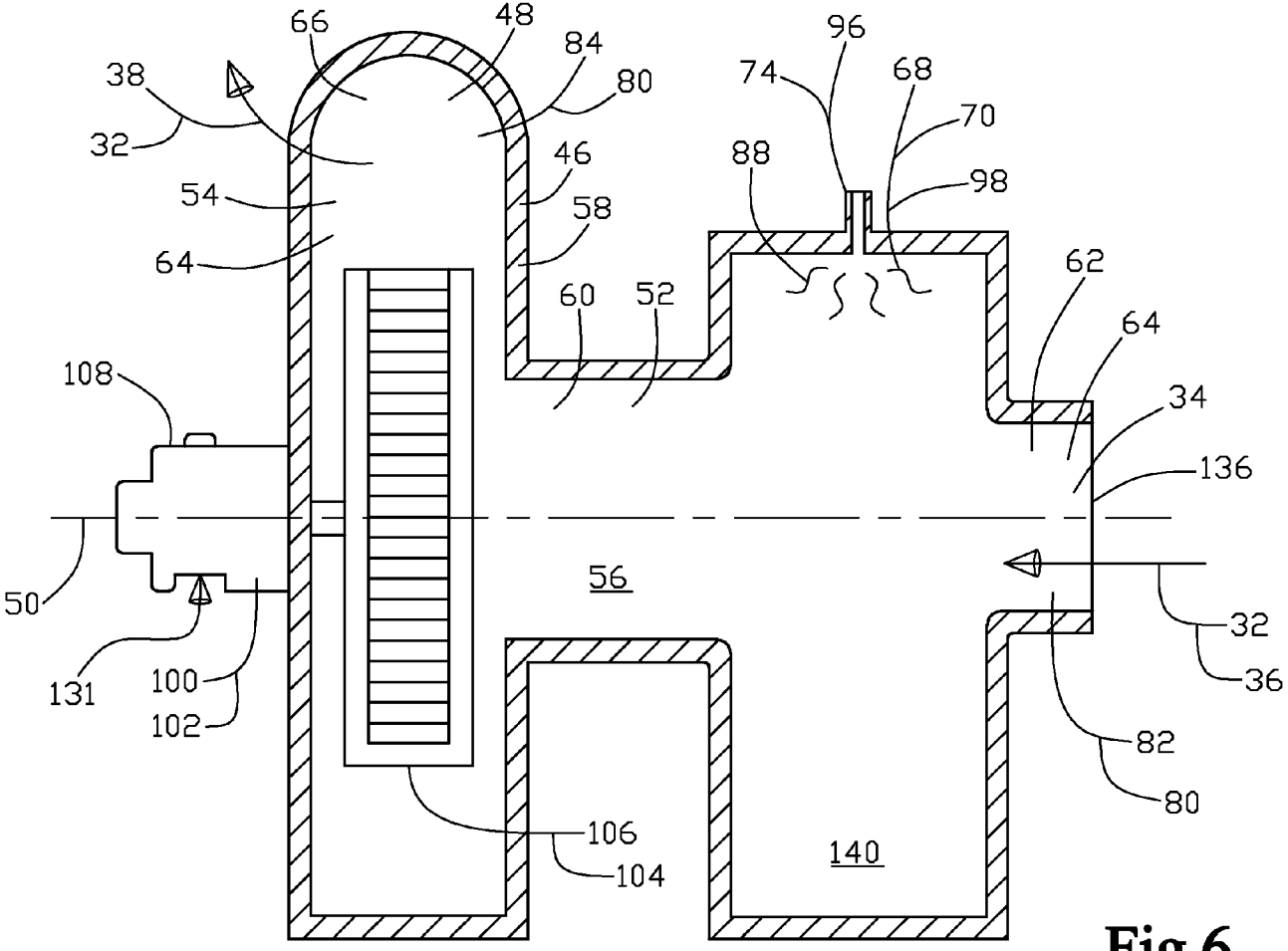
FIG. 6 shows a cross sectional side elevation view 6-6 from FIG. 1 of the fluid conditioning apparatus.
Figure 7:
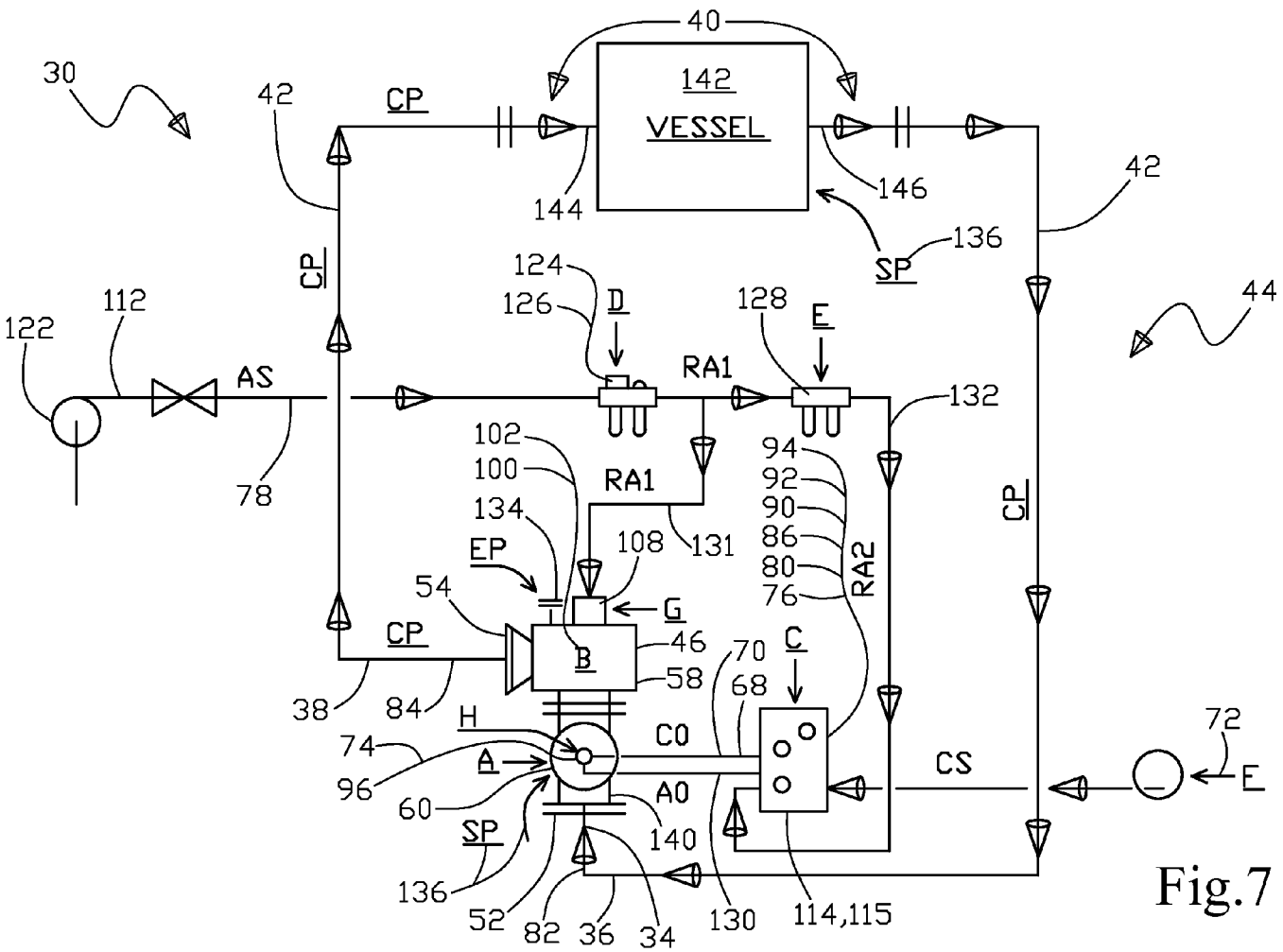
FIG. 7 shows an overall fluid schematic of the fluid conditioning apparatus including an adjacent vessel that is being conditioned to achieve a selected fluid condition in the vessel.
Figure 8:
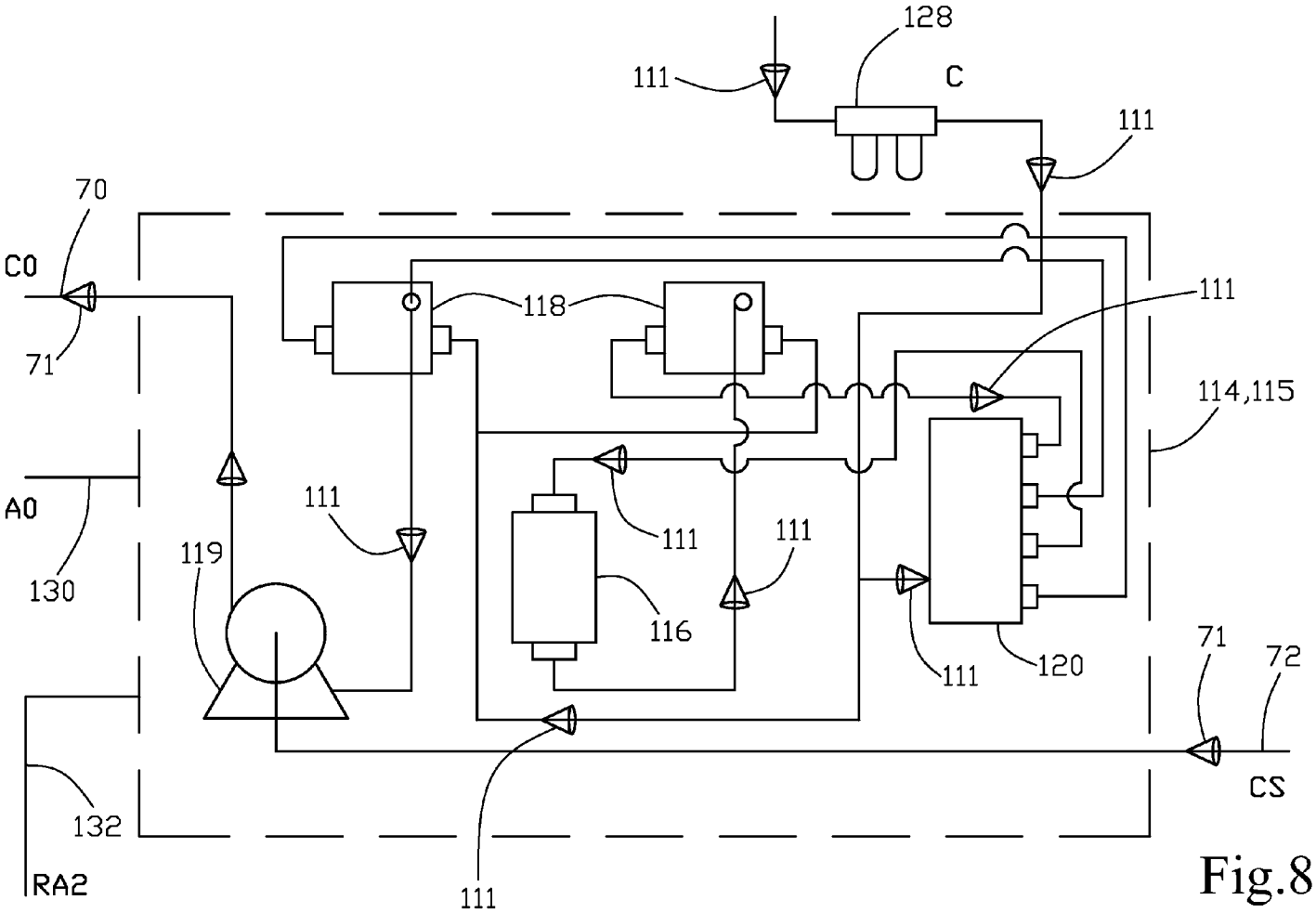
FIG. 8 shows a fluid schematic detail of the control box enclosure.
Figure 9:
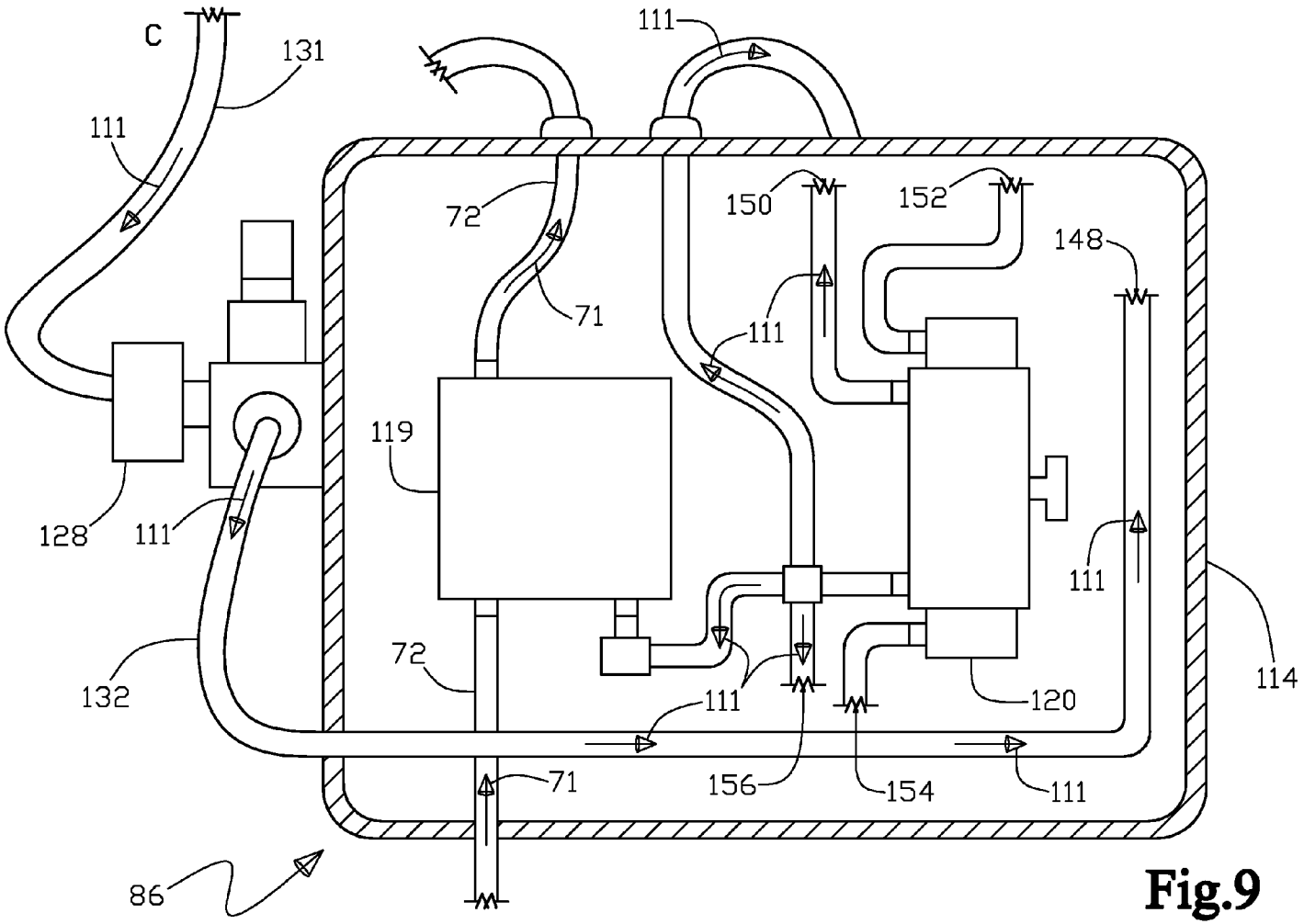
FIG. 9 shows a detail of the component arrangement within the control box enclosure body.
Figure 10:
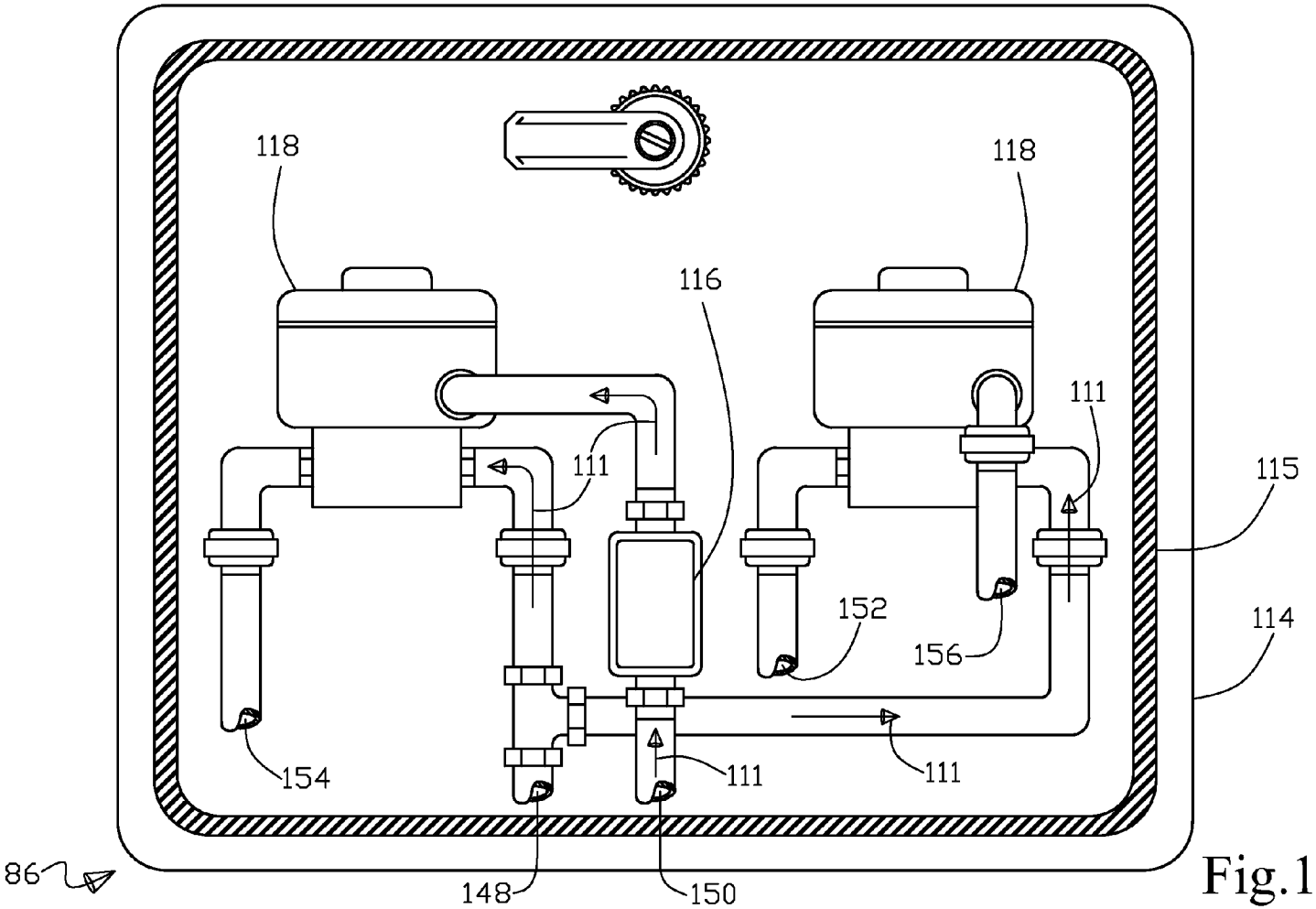
FIG. 10 shows a detail of the component arrangement within the control box enclosure cover.
Figure 11:
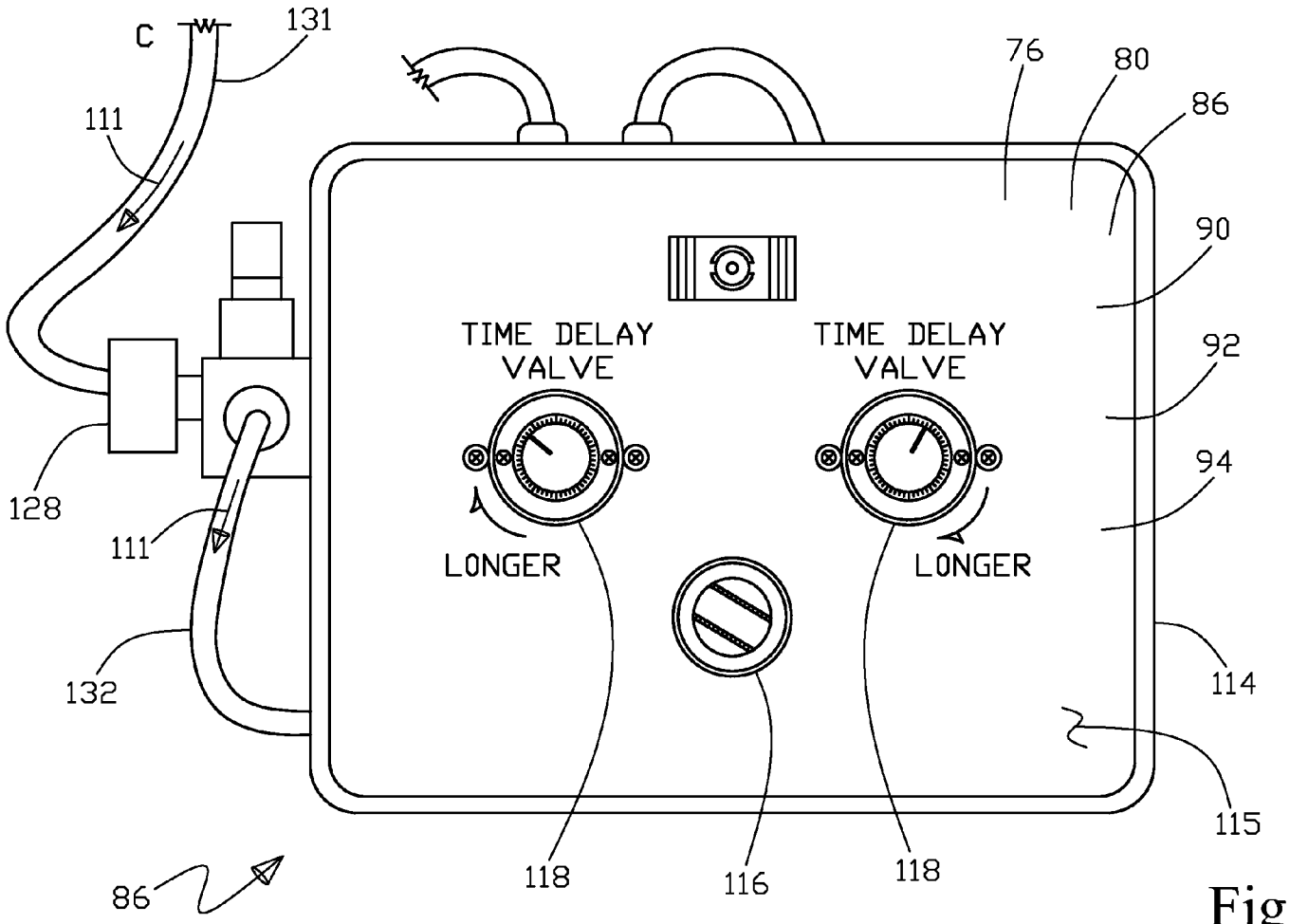
FIG. 11 shows a detail of the component arrangement disposed upon the control box cover.
Figure 12:
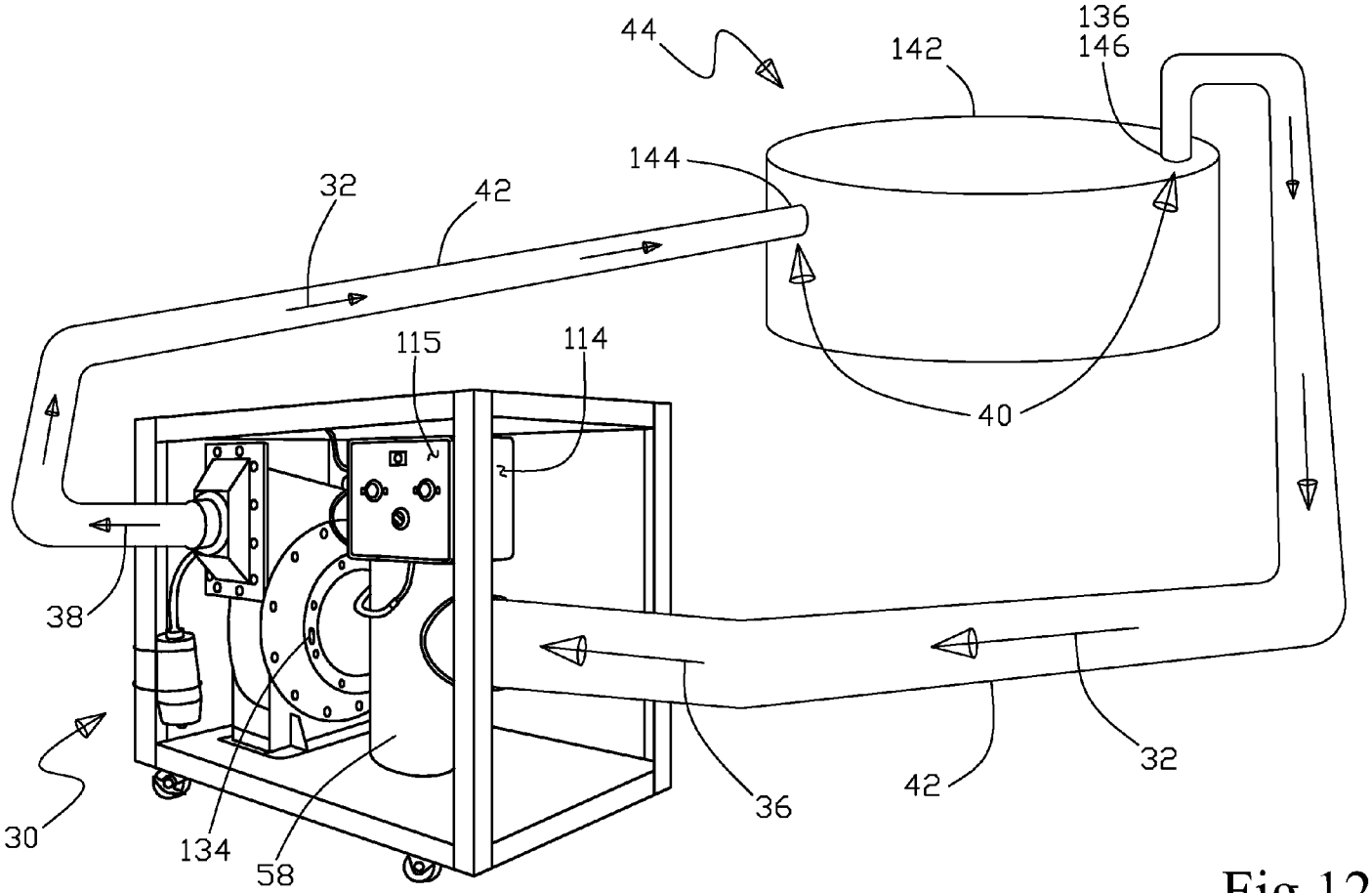
FIG. 12 shows a typical use application arrangement of the fluid conditioning apparatus with the vessel.
Figure 13:
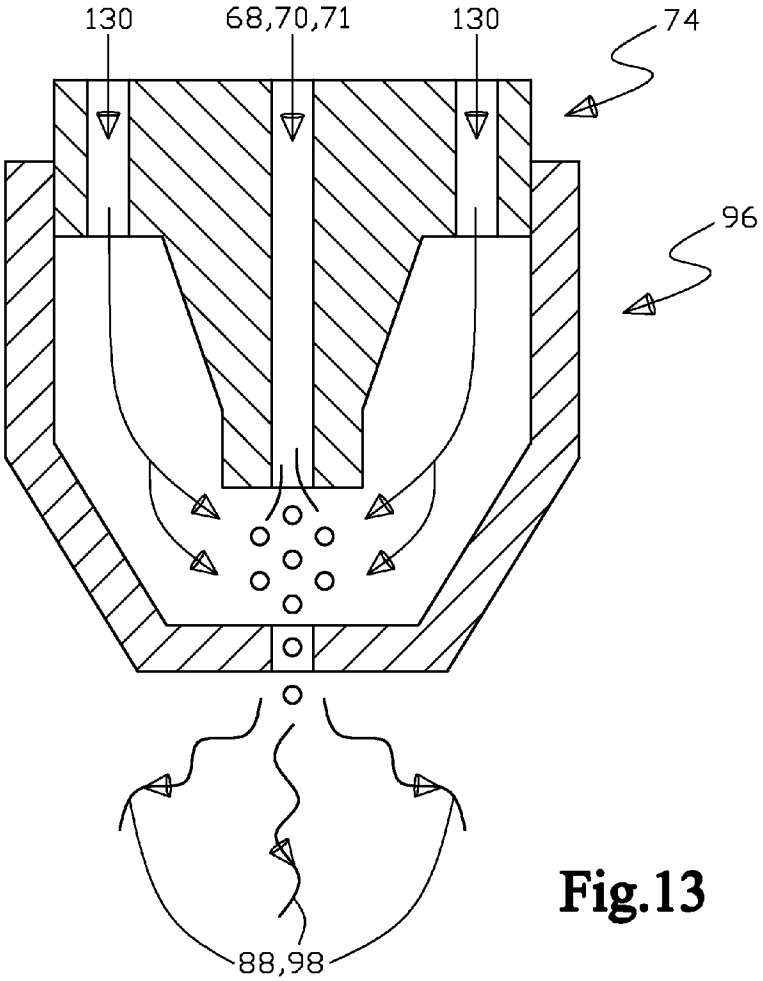
FIG. 13 shows a cross section of the nozzle for injection of the selected fluid into the fluid conditioning apparatus.

With initial reference to FIG. 1 shown is a perspective view of the fluid conditioning apparatus 30, FIG. 2 shows a side elevation view of the fluid conditioning apparatus 30, and FIG. 3 shows a cross sectional perspective view 3-3 from FIG. 1 of the fluid conditioning apparatus 30. Continuing, FIG. 4 shows a perspective view of the fluid conditioning apparatus 30 including the support structure 138 that the fluid conditioning apparatus 30 is disposed within, FIG. 5 shows a side elevation view of the fluid conditioning apparatus 30 including the support structure 138 from FIG. 4, and FIG. 6 shows a cross sectional side elevation view 6-6 from FIG. 1 of the fluid conditioning apparatus 30. Yet further, FIG. 7 shows an overall fluid schematic of the fluid conditioning apparatus 30 including an adjacent vessel 142 that is being conditioned to achieve a selected fluid 32 condition within the vessel 142 and FIG. 8 shows a fluid schematic detail of the control box enclosure body 114 and enclosure cover 115. Next, FIG. 9 shows a detail of the component arrangement within the control box enclosure body 114 and FIG. 10 shows a detail of the component arrangement within the control box enclosure cover 115. Continuing onward, FIG. 11 shows a detail of the component arrangement disposed upon the control box enclosure cover 115 and FIG. 12 shows a typical use application arrangement of the fluid conditioning apparatus 30 with the vessel 142 whose fluid 32 is being selectably conditioned. Further, FIG. 13 shows a cross section of the nozzle 96 for injection 98 of the selected fluid 70 into the fluid conditioning apparatus 30.

Broadly stated, in referring to FIGS. 1 to 11 the present invention of the fluid conditioning apparatus 30 that is for selectably conditioning 34 a fluid 32 disposed within the fluid conditioning apparatus 30, wherein the fluid conditioning apparatus 30 is in fluid communication 42 with a self contained or termed closed loop system in the form of a vessel 142, as shown in FIG. 12. Returning to FIGS. 1 to 11, the fluid conditioning apparatus 30 includes a housing 46 having a surrounding sidewall 48 positioned about a longitudinal axis 50, the surrounding sidewall 48 having an inlet portion 52 and an outlet portion 54. The sidewall 48, the inlet portion 52, and the outlet portion 54 all defining a housing interior 56, as best shown in FIGS. 3 and 6. Further included in the fluid conditioning apparatus 30 is a means 74 for disbursing a selected component 68 within the housing 46 interior 56 and a means 76 for controlling the selected component 68 disbursing to a achieve a selected fluid condition 34 ultimately within the vessel 142.

Starting with the housing 46, as best detailed in FIGS. 3 and 6, in-between the inlet portion 52 and the outlet portion 54 that respectively interface via the fluid communication 42 with the vessel 142 being specifically the vessel inlet portion 144 and the vessel outlet portion 146, essentially forming the self contained system 44, see FIG. 12 for the use view of the fluid conditioning apparatus 30 and basic layout of the self contained system. Returning to FIGS. 3 and 6, looking at particular at the housing 46 being termed a duct, it can be seen that there is the conditioning portion 60 being downstream from the selected component 68 injection point continuing toward the outlet portion 54, note that as shown with the means 100 for moving the fluid being optional, as the means 100 may exist outside of the housing 46 or even outside of the fluid conditioning apparatus 30, with the means 100 possibly being disposed within the fluid communication 42 or vessel 142. Just upstream from the housing conditioning portion 60 is the contamination portion 62 of the duct or being adjacent to the inlet portion 52 of the housing 46, thus being the point operationally where the fluid 32 communication is substantially directly from the vessel 142 via the fluid communication 42 as previously described. In addition a suction drum 140 is optionally provided to help knock out liquid components coming into the inlet portion 52 to help prevent damage to the means 100 for moving the fluid 32.

Continuing on the housing 46, there are also means 80 for monitoring the fluid 32 in what is termed sample points 136 on the housing 46 and the vessel 142, with the monitoring portion 64 of the duct being positioned adjacent to the inlet portion 52, wherein monitoring 82 at portion 64 is used to ascertain substantially the fluid 32 condition 36 in the vessel 142 or optionally directly monitoring the fluid 32 condition 36 at the vessel 142. Going further downstream with the flow of the fluid 32 within the housing 46, a testing portion 66 is positioned adjacent to the outlet portion 54, for monitoring 84, that is operationally used to ascertain the change in fluid 32 condition from the monitoring portion 64, with the information being used for control of means 74 for disbursing the selected component 68 and/or the means 76 for controlling the selected component 68 as subsequently described. Further to ensure anti-static properties of the housing 46, earth points 134 are provided for on the housing 46 and possibly on the fluid communication 42 or anywhere else the specific vessel 142 procedures require earth points 134. Looking at particular on the housing 46 the materials of construction are preferably aluminum, with alternatives of stainless steel, or any various composite type materials than may exhibit anti-static or other desired anti-corrosion properties. Other housing 46 materials would be acceptable providing that the functional characteristics of the alternative materials would be acceptable especially in the area of compatibility with the fluid 32 and the attendant environmental conditions such a corrosiveness, flammability, vessel 142 internal pressure, and the like.

Looking in detail at the selected component 68, which is typically a selected fluid 70 that is atomizable into the fluid 32 within the housing 46 interior 56 at the previously mentioned conditioning portion 60 of the duct or housing 46. However, note that the selected component 68 could be a solid, liquid or gas, or combination thereof. As best seen in FIGS. 7 and 8 schematically and FIGS. 1, 2, 4, and 5, the fluid 70 has a flow direction 71 as originating from a source 72. Note that the fluid 70 is preferably a liquid; however, it could also be in a gaseous form also. The fluid 70 is a selected chemical composition that is determined by the particular decontamination required within the vessel 142, and is preferably atomized to substantially be a dry vapor as it is communicated to the vessel 142.

Continuing, the means 76 for controlling is preferably operable by determining a volume of the component 68 disbursed resulting in a particular decontamination rate 40 of the system being the combination of the fluid conditioning apparatus 30, the vessel 142 and the adjacent fluid communication 42, see FIG. 12, wherein the means 76 further breaks down into the control 86 for adjusting the component 68 or typically being the selected fluid 70. The preferred method of accomplishing the means 76 is by the use of an air timer 118 in conjunction with an air operated pump 119, wherein the air timer 118 is operated at a selected setting for the timing period based upon achieving the selected fluid condition 34 ultimately within the vessel 142 as best shown in FIGS. 8 to 12. In addition, a power switch 116 controls the air supply between the air timers 118.

Continuing, the pneumatic timers 118, see FIG. 11, regulate the pneumatic air supply to the air pump 119 thereby controlling the pumping of the selected fluid 70 into the injector 96. Referring to FIG. 8 primarily, and also to FIGS. 9, 10, and 11, the timers 118 are in series to one another for their fluid communication signals, wherein the pilot valve 120 works by sending a signal to one of the timers 118 via the power switch 116, with the pilot valve 120 receiving a timed signal from a timer 118 which allows the pilot valve 120 to send a signal to the other series timer 118 and thus the liquid or selected fluid 70 initiating flow from pump 119. With the process being cyclical, with the other timer 118 adjacent to the pump 119 completing its time sequence, then the process starts again. Thus, the pulsing or stroke of the pump 119 is controllable through the adjustment of the timers 118.

An inline gas analyzer could be introduced that is in fluid communication with the duct 58 that would allow the treated vessel 142 fluid 32 when it reaches the desired outgoing fluid condition 38 to be released to the external (outside) environment. The air timer 118 is preferably a make and model number SMC-VR2110/VM13 or a suitable functional equivalent. The power switch 116 is preferably a make and model number SMC-VM4P or a suitable functional equivalent. Further, the pump 119 is preferably a make and model number SMC-PB1013-01 or a suitable functional equivalent. The means 76 that utilizes the air timer 118 and the pump 119 is principally schematically shown in FIG. 8 and physically shown in FIGS. 9-11 with the schematic association with the fluid conditioning apparatus 30 in overall schematic shown in FIG. 7. The selected pump 119 volume as measured in cubic centimeters per unit time and is in the range of about zero (0) to five-hundred (500) cubic-centimeters per hour (cc/hr). Further, the pilot valve 120 is preferably a make and model number SMC-SYA-5220-01 or a suitable functional equivalent.

Alternatively, the means 76 could be operable by cycling the component 68 disbursing to a higher and a lower volume over a time period, or in other words selectively pulsating 92 the component 68 volumetric flowrate, being operational to preferably add a greater degree of flexibility to the timing and amount of the selected component 68 that is disbursed within the housing interior 56, ultimately helping to move towards a more desired fluid 32 conditioning 34 within the vessel 142. Wherein, the pulsating of the component 68 would also be preferably accomplished by the aforementioned air timer 118 and the pump 119 by the control of the flow 111 of the gas or air to the pump 119. The selected pulsating volume of the pump 119 as measured in cubic centimeters per unit time with a no flow time period is in the range of about zero (0) to five-hundred (500) cubic-centimeters per hour (cc/hr).

Further, alternatively the means 76 for controlling could be operable by determining an allowable fluid 32 flowrate 94 therethrough the inlet portion 52 and the outlet portion 54. The fluid flowrate is best shown in FIG. 12 as the inlet fluid 32 condition 36 and moving toward the outlet fluid 32 condition 38 or this could be termed as the rate of fluid 32 conditioning or treatment. This flowrate is typically in the range of about 0.61 cubic meters per second (cm/s) or about 1,293 CFM, at a fan rotational speed of about 2,770 rpm, however, the flowrate could be more or less depending upon the application specifics such as vessel 142 contamination amount, the chemical makeup of the selected component 68, and the rate at which the selected component is dispersed within the fluid conditioning apparatus 30 interior 56. The method of controlling the fluid 32 flowrate through the fluid conditioning apparatus 30 can be accomplished by conventional valving either disposed within the housing 46 interior 56 or outside of housing 46 and adjacent to the fluid 32 communication 42 to or within the vessel 142 and/or by way of adjusting the volumetric flow rate of the means 100 for moving the fluid 32 from the inlet portion 52 to the outlet portion 54 being preferably by varying fan rotational speed (rpm) or alternative methods such as changing fan blades or any functional equivalent. The control for selecting the flowrate of the fluid 32 from the inlet portion 52 to the outlet portion 54 of the fluid conditioning apparatus 30 is determined from the fluid 32 achieving the selected condition at the incoming point 36 which substantially reflects the condition of the fluid 32 within the vessel 142, as opposed to the condition of the fluid 32 that is outgoing 38 that has typically the addition of the selected component 68. This determination of the fluid 32 condition can wither be done manually or in an automated fashion. Further, the means 76 for controlling the selected component 68 could be acceptably accomplished by components other that the aforementioned air timer 118 and pump 119 as long as the generally described function of the means 76 is maintained.

Continuing on the means 100 for moving the fluid 32 as best shown in FIG. 6, it is preferably adaptable for operation within a compressible fluid 32 as typically the fluid 32 is in gaseous form, and further as the fluid 32 can contain volatile, flammable, and/or toxic components the means 100 can be intrinsically safe in its operation being defined as not having the ability to provide a source of ignition to the fluid 32, with this entailing a multitude of design factors such as the non use of any electrical power, having non static electricity generating components, using micro power levels for signaling that do not reach an ignition threshold, and the like. The means 100 allows for a selected fluid 32 flowrate 94 through the housing 46. Thus, also preferably the dynamic component of the means 100 has anti-static 104 element properties, principally being the fan 106 portion that is disposed within the interior 56 of the duct 58 resulting in the means 102 for moving the fluid 32 in the interior 56 or within the duct 58. This results in the means 100 for moving the fluid 32 and the means 102 for moving the fluid 32 within the duct 58 are preferably an intrinsically safe fan 106 for use in hazardous atmospheres with a fan type of a CBI, at a rotational speed of 2770 RPM, having an Atex category of CE Ex II 3Gc with a rating of 0.61 cubic meters and pressure of 2,490 Pascals manufactured by Halifax fans. The fan itself can have brass rubbing strips, or brass positioned in potential contact/rub areas to minimize the chance of spark as an ignition source. The aforementioned fan being preferably driven by an air or gas motor 108 of about 3.6 HP at 130 CFM motor intake flowrate operating at 2,700 RPM, also preferably including an exhaust silencer 110 that is preferably a make and model Apro-SLD050 or suitable equivalent. Note that alternative fans and motors could be utilized that meet the previously described criteria or primarily operating in a compressible fluid and being intrinsically safe in operation.

Continuing, the means 74 for disbursing the selected component 68 as best shown in FIGS. 1 to 7 is preferably an injector 96, see FIG. 13 for cross sectional detail, that could also be termed an atomizer as preferably a brand GTC model number MWB 1520B1C that is disposed within the interior 56 of the housing 46, wherein operationally the means 74 atomizes the selected component 68 to be disbursed within the fluid 32 ultimately being for interaction with the fluid components originating from within the vessel 142 to achieve the selected fluid 32 condition 34. The selected injector 98 controls the atomization rate 88 of the selected fluid 70 and for determining a volume 90 of the selected component 68 of fluid 70 that is communicated 98 through the injector 96. However, other injectors could also be utilized that are similar in function to the GTC unit described above. Further, other components differentiated from the described injector 98 also could be utilized provided that they are operational to atomize the selected component 68 into the fluid 32 similar to the previously described means 74. In referring to FIGS. 4, 5, and 12, it can be seen that the fluid conditioning apparatus 30 has an optional support structure 138 that can be in the form of a frame that can "skid" the fluid conditioning apparatus 30 for enhanced portability and providing a mount for the control 86 via the enclosures 114 and 115, in addition to various other components such as the sound attenuation element 110 and other various components.

In looking at the previously described means 76 controlling, the means 74 for disbursing, and the means 100 for moving the fluid 32, all or a portion of can be a part of the same control system that is operable in an intrinsically safe manner, resulting in preferably a non-electrical system that is primarily disposed within the control 86 that is disposed within enclosure body 114 and enclosure cover 115 that is best shown schematically in FIGS. 7 and 8, and physically in FIGS. 9 and 10, and as incorporated into the fluid conditioning apparatus 30 in FIGS. 1, 2, 4, and 5. Thus, in the enclosure which includes the respective housing halves of the aforementioned enclosure body 114 and the enclosure cover 115 that contain the components of the pneumatic controller assembly 128, the gas driven pump 119, the pilot valve 120, the power switch 116, and the air timers 118. Wherein the means 78 for producing a selected gas pressure and flowrate preferably includes the source of the pneumatic energy from an air supply compressor 122 being considered as air supply 112 that feeds the primary air control 124 including the first regulated air supply 126 that branches off a line 131 that is in fluid communication with the motor 108 and continuing to the second regulated air supply 128 whose outlet is a line 132 that is in fluid communication with the enclosure body 114. In focusing on FIGS. 8 to 10 the direction of pneumatic gas flow being denoted by 111, that feeds the air pump 119, the pilot valve 120, and the air timers 118, with the power switch 116 controlling air between the air timers 118.

The injector 96, as best shown in FIG. 13 is disposed within the conditioning portion 60 receives a controlled air supply 130 from the control enclosure 86 and the controlled flow of the selected fluid 70 to facilitate the controlled or selected atomization rate 88 of the selected fluid 70 into the fluid 32 within the housing 46 interior 56 again for achieving a selected fluid 32 condition 43 within the vessel 142. The control of the atomization rate 88 of the selected fluid 70 is as previously described for the means 74 for disbursing and the means 76 for controlling that covers the flowrate of the selected fluid 70 through the injector 96 and the optional pulsation of the fluid 70 flowrate through the injector 96. Further, an optional control system can monitor the fluid 32 between the inlet portion 52 and the outlet portion 54 to adjust the selected fluid 70 injection into the fluid 32 that is disposed within the housing 56 volumetrically and/or pulsation wise in possible conjunction with the fan 106 fluid 32 flowrate to automate the fluid conditioning apparatus 30 into a system for automatically achieving the selected fluid 32 condition 34 within the vessel 142.

What this results in is that the means 76 for controlling the selected component 68 as related to achieving the selected fluid condition 34 in the vessel 142 is all facilitated in an intrinsically safe manner, and in this particular embodiment without the use of electrical power or signaling, thus eliminating the source for ignition, allowing the fluid conditioning apparatus 30 to operate in flammable or hazardous environments. Thus, in a specific embodiment sense, control of the injector 96 fluid 70 flowrate and pulsation, in addition to the fan 106 are all done in an intrinsically safe manner by not having either electrical power or signaling present via the use of pneumatic air for both power and signaling purposes.

Method of Use

Referring in particular to FIG. 12 showing the fluid conditioning apparatus 30 in use, a method for using the fluid conditioning apparatus is disclosed that includes the steps of firstly of providing the fluid conditioning apparatus 30 that includes a housing 46 having a surrounding sidewall 48 positioned about a longitudinal axis 50. With the surrounding sidewall 48 having an inlet portion 52 and an outlet portion 54, resulting in the sidewall 48, inlet portion 52, and outlet portion 54 all defining the housing interior 56. Further included in the fluid conditioning apparatus 30 is the means 74 for disbursing 88 the selected component 68 within the housing 46 interior. Also further included in the fluid conditioning apparatus 30 is the means 76 for controlling the selected component 68 disbursing 88 to achieve the selected fluid condition 34 in addition to providing the means 100 for moving the fluid 32. Wherein the fluid conditioning apparatus 30 itself is best shown in a detailed manner in FIGS. 1 to 11.

Continuing, in returning to reference FIG. 12, as local conditions require, the fluid communication 42 lines would be interconnected as between the fluid conditioning apparatus 30 and the vessel 142, resulting in a closed loop or self contained system 44, wherein the fluid communication is grounded electrically having an earth point if required by local codes. Further to this on the fluid conditioning apparatus 30 itself the earth point 134, see FIGS. 2 and 5, would be placed in electrical communication with an applicable grounding point. Wherein the vessel 142 would need degassing or other decontamination, with a typical example being the undesirable presence of flammable or hazardous vapors residing within the vessel, wherein the vessel has been emptied of its original fluid for repair, cleaning and the like. Of course there is an environmental impact to be considered if these undesirable vessel 142 gases were simply purged out into the atmosphere without any type of treatment, thus neutralizing to an extent the environmentally adverse properties of these flammable and/or hazardous gases is in important consideration. Thus, in a closed system or as being termed a self contained system 44, removes the requirement for air or another medium to be introduced into the treatment area to replace the external environment atmosphere as it is being taken out of or moved through the system. This results in the present system being able to draw off vapor from the vessel 142 needing treatment then conditioning it through the fluid conditioning apparatus 30 and eventually releasing it to the atmosphere when the treatment is completed.

Further, a next step is activating the means 100 for moving the fluid 32 that is preferably in the form of the air operated motor 108 that is rotationally coupled to the fan 106 to initiate the movement of the fluid 32 within the closed loop or self contained system 44 as shown in FIG. 12. Note that as previously described the means 100 for moving the fluid 32 is also preferably set up to operate in an intrinsically safe manner, i.e. being operable in a flammable environment as the fan motor 108 is air driven and the fan 106 itself is constructed of a non-sparking material in conjunction with having anti-static generation properties. Note that the volumetric rate at which the fluid 32 is moved within the fluid conditioning apparatus 30, the fluid communication 42 and the vessel 142 can optionally be variable as operationally altering the introduction of the selected component 68 or fluid 70 into the vessel 142. The variable volumetric rate for the fluid 32 by of the means 100 for moving the fluid 32 can be accomplished by controlling the amount of air feed into the motor 108 and thus the motor 108 RPM and fan 106 RPM, alternatively or in combination the fan 106 be adjustable or interchanged with a fan 106 of a different size that would also result in a different volumetric rate for the fluid 32.

Continuing, a next step is in activating the selected component 68 disbursing within the interior 56 of the housing 46, which is to essentially control the selected fluid 70 being the preferred portion of the selected component 68 introduction into the fluid 32 that in turn interacts with the typically undesirable gases present within the vessel 142 to condition these gases to help make the vessel 142 safe for its planned repair, cleaning, or maintenance and to treat these undesirable gases so as to be environmentally acceptable. In initially using the control 86 that is housed in the enclosure body portion 114 and it's mating enclosure cover 115 as best shown in FIGS. 8 to 11, the control 86 or means 76 for controlling the selected component 68 or preferably selected fluid 70, wherein the means 76 preferably includes pneumatic timers 118 and the air pump 119, wherein the selected fluid 70 is regulated as to dosing or volume 90 length/cycle or pulsing 92 of the selected fluid 70 as atomized 88 through the nozzle injector 96 into the fluid 32 stream within the housing 46.

This is accomplished by adjusting the pneumatic timers 118, see FIG. 11, that in turn regulate the air supply to the air pump 119 thereby controlling the pumping of the selected fluid 70 into the injector 96. Referring to FIG. 8 primarily, and also to FIGS. 9, 10, and 11, the timers 118 are operable to be in series to one another for their fluid communication signals, wherein the pilot valve 120 works by sending a signal to one of the timers 118 via the power switch 116, with the pilot valve 120 receiving a timed signal from a timer 118 which allows the pilot valve 120 to send a signal to the other series timer 118 and thus the liquid or selected fluid 70 initiating flow from the pump 119, with the process being cyclical with the other timer 118 adjacent to the pump 119 completing its time sequence, then the process starts again. Thus, the pulsing or stroke of the pump 119 is controllable through the adjustment of the timers 118. Once the means 100 to move the fluid 32 is activated and the selected fluid 70 is regulated as to dosing or volume 90 length/cycle or pulsing 92 of the selected fluid 70 the process is continued for a period known as the monitoring step to achieve the selected fluid condition 34 after a selected time period. It can be possible to engage in using the control 86 including the means 76 to readjust multiple times the selected fluid 70 being regulated as to dosing or volume 90 length/cycle or pulsing 92 of the selected fluid 70 in the process in being continued for a period known as the monitoring step and the using step in combination to further achieve the selected fluid condition 34 in the vessel. Additionally, additional injector 96 points could be added at various selected points within the fluid conditioning apparatus 30, fluid communication 42, and/or the vessel 142 as desired with each of their accompanying control 86 systems as previously described or with the multiple injectors 96 operating from a central control 86 system.

As a further optional refinement of the monitoring step, when monitoring the selected fluid condition 34 further comprises monitoring an outgoing fluid condition 38 at the outlet portion 54 and monitoring an incoming fluid condition 36 at the inlet portion 52 that is operational to ascertain a decontamination rate of the system or defined as achieving the selected fluid condition 34 within the vessel 142, thus allowing the use of the fluid conditioning apparatus 30 to stop. However, there could be a situation that even after achieving the selected fluid condition 34 with the fluid conditioning apparatus 30 there may be a dwell time period to re-test the fluid 32 for undesired flammable, hazardous, or other properties and possibly re-initiate the use of the fluid conditioning apparatus 30 as previously described. When the selected fluid condition 34 is finally achieved without the need for remonitoring of the selected fluid condition 34 then the fluid communication 42 can be removed from the vessel and atmospheric air or the environmental atmosphere can be introduced into the vessel 142.

CONCLUSION

Accordingly, the present invention of a fluid conditioning apparatus 30 has been described with some degree of particularity directed to the embodiment(s) of the present invention. It should be appreciated, though; that the present invention is defined by the following claims construed in light of the prior art so modifications or changes may be made to the exemplary embodiment(s) of the present invention without departing from the inventive concepts contained therein.

The invention claimed is:

1. A fluid conditioning apparatus to selectably condition a fluid disposed within a vessel, wherein said fluid conditioning apparatus is in closed loop fluid communication with the vessel, said fluid conditioning apparatus comprising:

(a) a closed loop fluid duct including a conditioning portion, a contamination portion, a monitoring portion, an inlet portion, and an outlet portion to define a fluid duct interior, said inlet portion is in closed fluid communication with an outlet portion of the vessel, and said outlet portion is in closed fluid communication with an inlet portion of the vessel to define a self contained closed loop system;

(b) a source of a selected liquid;

(c) a compressor for producing a pneumatic energy source resulting in a selected gas pressure and flow;

(d) an injector adjacent to said conditioning portion, said injector in fluid communication with said source of the selected liquid and said compressor for producing a selected gas pressure and flow;

(e) a means for moving the fluid that is disposed within said duct;

(f) a means for monitoring the fluid that is in fluid communication with said duct inlet portion to operationally monitor the fluid disposed within the vessel; and (g) a control for adjusting the selected liquid desired atomization rate and pulsation cycles in conjunction with determining an allowable inlet condition of the fluid from said duct inlet portion as determined by helping to achieve the selected condition of the fluid, wherein operationally to determine if the fluid disposed within the vessel needs further conditioning via recycling in the self contained closed loop system or the fluid is sufficiently conditioned to be released to the external outside environment.

2. A fluid conditioning apparatus according to claim 1 further comprising a support structure for said duct.

3. A fluid conditioning apparatus according to claim 1 wherein said duct inlet portion further comprises a suction drum.

4. A fluid conditioning apparatus according to claim 1 wherein said means for moving the fluid is constructed of a fan that is motor driven, wherein said motor is powered by an energy source selected from the group consisting of pressurized air and pressurized gas.

5. A fluid conditioning apparatus according to claim 4 wherein said fan is constructed of brass in a potential contact area to operationally minimize the potential for a spark as between said fan and said fluid duct interior.

6. A fluid conditioning apparatus according to claim 1 wherein said duct further comprises a testing portion that is operable to monitor the fluid at said duct outlet portion in conjunction with said means for monitoring the fluid at said inlet portion to provide control feedback on a change in the fluid condition as the fluid passes through the vessel.

[7. A method for using a fluid conditioning apparatus to selectably condition a fluid disposed within a vessel, wherein said fluid conditioning apparatus is in closed loop fluid communication with the vessel, said method for using said fluid conditioning apparatus comprising the steps of:

(a) providing a fluid conditioning apparatus that includes a housing having a surrounding sidewall positioned about a longitudinal axis, said surrounding sidewall having an inlet portion and an outlet portion, said sidewall, inlet portion, and outlet portion defining a housing interior, said inlet portion is in closed fluid communication with an outlet portion of the vessel, and said outlet portion is in closed fluid communication with an inlet portion of the vessel to define a self contained closed loop system, a means for disbursing a selected component within said housing interior, and a means for controlling said selected component disbursing to a achieve the selected fluid condition at said fluid conditioning apparatus inlet portion to operationally monitor the fluid disposed within the vessel;

(b) activating said selected component disbursing;

(c) monitoring said selected fluid condition after a selected time period;

(d) using said means for controlling to determine said selected component disbursing amount based upon moving toward achieving the selected fluid condition;

(e) continuing to condition the fluid to determine if the fluid disposed within the vessel needs further conditioning via recycling in the self contained closed loop system; and (f) determining if the fluid is sufficiently conditioned to be released to the external outside environment.]

*8. A fluid conditioning apparatus to selectably condition a fluid disposed within a vessel, wherein said fluid conditioning apparatus is in closed loop fluid communication with the vessel, said fluid conditioning apparatus comprising:*

*(a) a housing having a surrounding sidewall positioned about a longitudinal axis, said surrounding sidewall having an inlet portion and an outlet portion, said sidewall, inlet portion, and outlet portion defining a housing interior, said inlet portion is in closed fluid communication with an outlet portion of the vessel, and said outlet portion is in closed fluid communication with an inlet portion of the vessel to define a self-contained closed loop system;*

*(a1) a compressor constructed of an air pump including an air timer for producing a pneumatic energy source resulting in a selected air pressure and flow;*

*(b1) an injector in fluid communication with said compressor and with said housing interior, wherein said injector operationally disburses a selected component within said housing interior; and*

*(c) a means for continuous controlling said selected component disbursing to achieve a selected fluid condition at said inlet portion via said air timer being operated at a selected setting for a timing period to operationally monitor the fluid disposed within the vessel, wherein operationally to determine if the fluid disposed within the vessel needs further conditioning via recycling in the self-contained closed loop system or the fluid is sufficiently conditioned to be released to the external outside environment.*

* * * * *